United States Patent
Lu et al.

(10) Patent No.: US 12,064,179 B2
(45) Date of Patent: Aug. 20, 2024

(54) METHOD FOR OPERATING NEAR-EYE DISPLAY DEVICE AND NEAR-EYE DISPLAY DEVICE

(71) Applicant: Coretronic Corporation, Hsin-Chu (TW)

(72) Inventors: Chih-Hung Lu, Hsin-Chu (TW); Chung-Jen Ou, Hsin-Chu (TW)

(73) Assignee: Coretronic Corporation, Hsin-Chu (TW)

(*) Notice: Subject to any disclaimer, the term of this patent is extended or adjusted under 35 U.S.C. 154(b) by 0 days.

(21) Appl. No.: 18/299,058

(22) Filed: Apr. 12, 2023

(65) Prior Publication Data

US 2023/0329545 A1     Oct. 19, 2023

(30) Foreign Application Priority Data

Apr. 14, 2022   (TW) .................. 111114200

(51) Int. Cl.
*A61B 3/00*  (2006.01)
*A61B 3/10*  (2006.01)

(52) U.S. Cl.
CPC .............. *A61B 3/0025* (2013.01); *A61B 3/10* (2013.01); *A61B 3/0041* (2013.01)

(58) Field of Classification Search
None
See application file for complete search history.

(56) References Cited

U.S. PATENT DOCUMENTS

| 10,426,668 B2* | 10/2019 | Maeda | G06T 3/40 |
| 11,696,073 B2* | 7/2023 | Spector | G06F 3/165 |
| | | | 455/3.06 |
| 11,857,259 B2* | 1/2024 | Raymond | A61B 3/135 |
| 2017/0000341 A1* | 1/2017 | Samec | A61B 3/1015 |
| 2020/0397288 A1 | 12/2020 | Zidan et al. | |
| 2021/0257084 A1 | 8/2021 | Freeman et al. | |
| 2021/0290053 A1* | 9/2021 | Tran | A61B 3/113 |
| 2023/0218163 A1* | 7/2023 | Hunter | A61B 3/032 |
| | | | 351/213 |

FOREIGN PATENT DOCUMENTS

| CN | 107526165 | 12/2017 |
| CN | 111616672 | 9/2020 |
| TW | I697692 | 7/2020 |
| TW | 202119093 | 5/2021 |
| TW | 740561 | 9/2021 |

OTHER PUBLICATIONS

"Office Action of Taiwan Counterpart Application", issued on Apr. 26, 2023, p. 1-p. 13.

* cited by examiner

*Primary Examiner* — Duane N Taylor, Jr.
(74) *Attorney, Agent, or Firm* — JCIPRNET

(57) ABSTRACT

A method for operating a near-eye display device is provided, which includes: disposing the near-eye display device in front of an eye of a user; forming a display image through the near-eye display device; changing the display image to perform a short-distance vision examination on the eye; changing the display image to perform a long-distance vision examination on the eye; obtaining vision examination data of the user according to results of the short-distance vision examination and the long-distance vision examination, and storing the vision examination data; and according to the vision examination data, adjusting a system parameter of the near-eye display device.

5 Claims, 11 Drawing Sheets

ɯ   Ǝ   ო   E   ɯ   20/30

E   Ǝ   ᛖ   E   ɯ   20/25

ო   ɯ   Ǝ   E   ო   20/20

METHOD FOR OPERATING NEAR-EYE DISPLAY DEVICE AND NEAR-EYE DISPLAY DEVICE

CROSS-REFERENCE TO RELATED APPLICATION

This application claims the priority benefit of Taiwan application serial no. 111114200, filed on Apr. 14, 2022. The entirety of the above-mentioned patent application is hereby incorporated by reference herein and made a part of this specification.

BACKGROUND

Technical Field

The disclosure relates to a method for operating a near-eye display device and a near-eye display device.

Description of Related Art

The demand for extended reality (XR) systems is increasing day by day. In actual use, various extended reality systems need to be adjusted according to the vision of a user, so that the user can obtain the best visual effect.

In the virtual reality system, for monocular vision, the zoom lens may be configured to change the focal length of the lens, so as to correct the spherical aberration of vision, that is, the diopter, so that the image viewed by the user is clear. However, for binocular vision, in addition to spherical aberration, astigmatism and eye position also need to be corrected, so that the user can view a clear image and normal binocular fusion is generated.

The information disclosed in this Background section is only for enhancement of understanding of the background of the described technology and therefore it may contain information that does not form the prior art that is already known to a person of ordinary skill in the art. Further, the information disclosed in the Background section does not mean that one or more problems to be resolved by one or more embodiments of the invention was acknowledged by a person of ordinary skill in the art.

SUMMARY

The disclosure provides a method for operating a near-eye display device and a near-eye display device, which can complete the exam of the vision of a user by an exam of the human eye standard and a subsequent correction procedure, while achieving the correction of the near-eye display device, so that the user can see a clear image.

Other objectives and advantages of the disclosure can be further understood from the technical features disclosed in the disclosure.

In order to achieve one, a part, or all of the above objectives or other objectives, an embodiment of the disclosure provides a method for operating a near-eye display device, which includes the following steps. The near-eye display device is disposed in front of an eye of a user to form a display image through the near-eye display device. The display image is changed to perform a short-distance vision examination on the eye. The display image is changed to perform a long-distance vision examination on the eye. Vision examination data of the user is obtained according to results of the short-distance vision examination and the long-distance vision examination, and the vision examination data is stored. According to the vision examination data, a system parameter of the near-eye display device is adjusted.

In an embodiment of the disclosure, the step of changing the display image to perform the short-distance vision examination on the eye includes a first short-distance binocular image fusion exam; a short-distance diopter exam; a short-distance adjustment amplitude exam; a short-distance eye position exam; and a second short-distance binocular image fusion exam.

In an embodiment of the disclosure, the step of the first short-distance binocular image fusion exam includes setting positions of multiple optotypes at a distance of 40 cm from the eye to project the display image to the eye. The display image includes the optotypes. When binocular fusion is generated, the long-distance vision examination is performed, and when binocular fusion is not generated, the short-distance diopter exam is performed.

In an embodiment of the disclosure, the step of the short-distance diopter exam includes setting positions of multiple optotypes at a distance of 40 cm from the eye to project the display image to the eye. The display image includes the optotypes. When a vision of the eye is greater than or equal to 0.8, the short-distance adjustment amplitude exam is performed, and when a vision of the eye is less than 0.8, a diopter exam is performed on the eye to measure an astigmatism of the eye, and corrective lenses are placed or a front/rear position of the display image is changed according to a result of the diopter exam, so that the vision of the eye is greater than or equal to 0.8. After placing the corrective lenses or changing the position of the display image, so that the vision of the eye is greater than or equal to 0.8, when binocular fusion is generated, the long-distance vision examination is performed, and when binocular fusion is not generated, the short-distance adjustment amplitude is performed.

In an embodiment of the disclosure, the step of the short-distance adjustment amplitude exam includes projecting the display image to the eye to examine a closest visible focus distance of the eye of the user. When the closest visible focus distance is a normal value, the short-distance eye position exam is performed, and when the closest visible focus distance is an abnormal value, corrective lenses are placed or a front/rear position of the display image is changed, so that the closest visible focus distance is the normal value. After placing the corrective lenses or changing the position of the display image, so that the closest visible focus distance is the normal value, when binocular fusion is generated, the long-distance vision examination is performed, and when binocular fusion is not generated, the short-distance eye position exam is performed.

In an embodiment of the disclosure, the step of the short-distance eye position exam includes projecting the display image to the eye to examine short-distance horizontal eye position information and short-distance vertical eye position information of the user. When the short-distance horizontal eye position information and the short-distance vertical eye position information are normal values, the second short-distance binocular image fusion exam is performed, and when the short-distance horizontal eye position information or the short-distance vertical eye position information is an abnormal value, corrective lenses are placed or a front/rear position of the display image is changed, so that the short-distance horizontal eye position information and the short-distance vertical eye position information are adjusted to the normal values. After changing the position of the display image, so that the short-distance horizontal eye position information and the short-distance vertical eye position information are the normal values, when binocular fusion is generated, the long-distance vision examination is performed, and when binocular fusion is not generated, the second short-distance binocular image fusion exam is performed.

In an embodiment of the disclosure, the step of the second short-distance binocular image fusion exam includes setting positions of multiple optotypes at a distance of 40 cm from the eye to project the display image to the eye to examine a short-distance fusion ability of the user. The display image includes the optotypes. When the short-distance fusion ability is a normal value, an optometry advice is provided to the user, and when the short-distance fusion ability is an abnormal value, a customer service is sought, and the exam is stopped.

In an embodiment of the disclosure, the step of changing the display image to perform the long-distance vision examination on the eye includes a first long-distance binocular image fusion exam; a long-distance diopter exam; a long-distance eye position exam; and a second long-distance binocular image fusion exam.

In an embodiment of the disclosure, the step of the first long-distance binocular image fusion exam includes setting positions of multiple optotypes at a distance of 6 meters from the eye to project the display image to the eye. The display image includes the optotypes. When binocular fusion is generated, the exam ends, and when binocular fusion is not generated, the long-distance vision examination is performed.

In an embodiment of the disclosure, the step of the long-distance diopter exam includes setting positions of multiple optotypes at a distance of 6 meters from the eye to project the display image to the eye. The display image includes the optotypes. When a vision of the eye is greater than or equal to 0.8, the long-distance eye position exam is performed, and when a vision of the eye is less than 0.8, a diopter exam is performed on the eye to measure an astigmatism of the eye, and corrective lenses are placed or a front/rear position of the display image is changed according to a result of the diopter exam, so that the vision of the eye is greater than or equal to 0.8. After placing the corrective lenses or changing the position of the display image, so that the vision of the eye is greater than or equal to 0.8, when binocular fusion is generated, the exam ends, and when binocular fusion is not generated, the long-distance eye position exam is performed.

In an embodiment of the disclosure, the step of the long-distance eye position exam includes projecting the display image to the eye to examine long-distance horizontal eye position information and long-distance vertical eye position information of the user. When the long-distance horizontal eye position information and the long-distance vertical eye position information are normal values, the second long-distance binocular image fusion exam is performed, and when the long-distance horizontal eye position information or the long-distance vertical eye position information is an abnormal value, corrective lenses are placed or a front/rear position of the display image is changed, so that the long-distance horizontal eye position information and the long-distance vertical eye position information are adjusted to the normal values. After changing the position of the display image, so that the long-distance horizontal eye position information and the long-distance vertical eye position information are the normal values, when binocular fusion is generated, the exam ends, and when binocular fusion is not generated, the second long-distance binocular image fusion exam is performed.

In an embodiment of the disclosure, the step of the second long-distance binocular image fusion exam includes setting positions of multiple optotypes at a distance of 6 meters from the eye to project the display image to the eye to examine a long-distance fusion ability of the user. The display image includes the optotypes. When the long-distance fusion ability is a normal value, an optometry advice is provided to the user, and when the long-distance fusion ability is an abnormal value, a customer service is sought, and the exam is stopped.

In an embodiment of the disclosure, the vision examination data includes a diopter, an astigmatism, an eye position, and a combination thereof.

In an embodiment of the disclosure, the method for operating further includes the following steps. Through an operation interface of the near-eye display device, the vision examination data is input to the near-eye display device to store the vision examination data through a storage element of the near-eye display device. The vision examination data is loaded through the operation interface to adjust a system parameter of the near-eye display device according to the vision examination data.

In order to achieve one, a part, or all of the above objectives or other objectives, an embodiment of the disclosure provides a near-eye display device, which is disposed in front of an eye of a user. The near-eye display device includes a display, configured to emit an image beam; a lens array, disposed on a transmission path of the image beam and located between the display and the eye; at least one lens, disposed on the transmission path of the image beam and located between the display and the eye, wherein the image beam is projected to the eye via the lens array and the at least one lens to form a display image; and a processor, coupled to the display, wherein the processor is configured to change the display image to perform a short-distance vision examination on the eye, change the display image to perform a long-distance vision examination on the eye, and obtain vision examination data of the user according to results of the short-distance vision examination and the long-distance vision examination, and store the vision examination data, and adjust a system parameter of the near-eye display device according to the vision examination data.

In an embodiment of the disclosure, the short-distance vision examination includes a first short-distance binocular image fusion exam; a short-distance diopter exam; a short-distance adjustment amplitude exam; a short-distance eye position exam; and a second short-distance binocular image fusion exam.

In an embodiment of the disclosure, the long-distance vision examination includes a first long-distance binocular image fusion exam; a long-distance diopter exam; a long-distance eye position exam; and a second long-distance binocular image fusion exam.

In an embodiment of the disclosure, the near-eye display device further includes a storage element, configured to store the vision examination data. The processor is further configured to read the vision examination data from the storage element.

In an embodiment of the disclosure, the near-eye display device further includes an operation interface, configured to allow the user to input the vision examination data to the near-eye display device through the operation interface, and to load the vision examination data through the operation interface to adjust a system parameter of the near-eye display device according to the vision examination data.

Based on the above, by using the near-eye display device to examine the vision of the user, obtaining the vision examination data of the user, and adjusting the optical system of the near-eye display device according to the vision examination data of the user, the user can have a better usage experience.

In order for the features and advantages of the disclosure to be more comprehensible, the following specific embodiments are described in detail in conjunction with the drawings.

Other objectives, features and advantages of the invention will be further understood from the further technological features disclosed by the embodiments of the invention wherein there are shown and described preferred embodiments of this invention, simply by way of illustration of modes best suited to carry out the invention.

Figure 1:
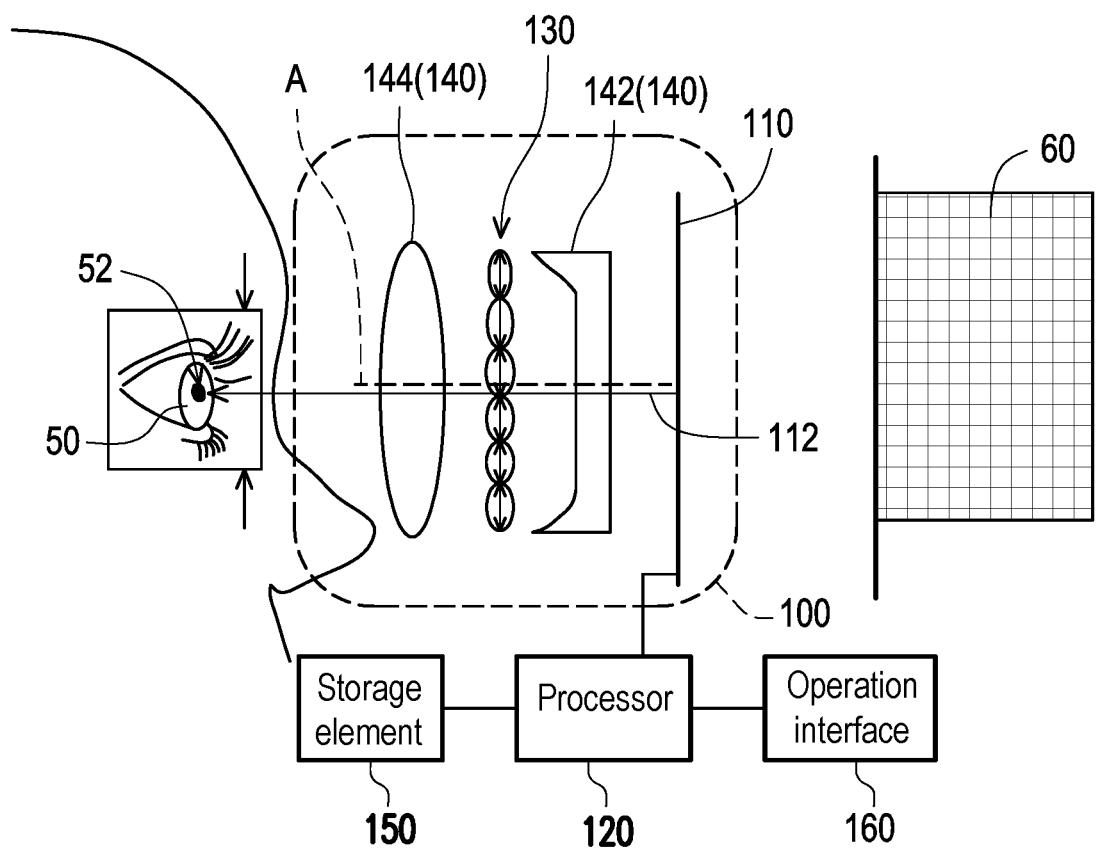
FIG. 1 is a schematic diagram of a near-eye display device according to an embodiment of the disclosure.

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION OF DISCLOSED EMBODIMENTS

In the following detailed description of the preferred embodiments, reference is made to the accompanying drawings which form a part hereof, and in which are shown by way of illustration specific embodiments in which the invention may be practiced. In this regard, directional terminology, such as "top," "bottom," "front," "back," etc., is used with reference to the orientation of the Figure(s) being described. The components of the present invention can be positioned in a number of different orientations. As such, the directional terminology is used for purposes of illustration and is in no way limiting. On the other hand, the drawings are only schematic and the sizes of components may be exaggerated for clarity. It is to be understood that other embodiments may be utilized and structural changes may be made without departing from the scope of the present invention. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. Similarly, the terms "facing," "faces" and variations thereof herein are used broadly and encompass direct and indirect facing, and "adjacent to" and variations thereof herein are used broadly and encompass directly and indirectly "adjacent to". Therefore, the description of "A" component facing "B" component herein may contain the situations that "A" component directly faces "B" component or one or more additional components are between "A" component and "B" component. Also, the description of "A" component "adjacent to" "B" component herein may contain the situations that "A" component is directly "adjacent to" "B" component or one or more additional components are between "A" component and "B" component. Accordingly, the drawings and descriptions will be regarded as illustrative in nature and not as restrictive.

The foregoing and other technical contents, features, and effects of the disclosure will be clearly presented in the following detailed description of a preferred embodiment with reference to the drawings. The directional terms, such as up, down, left, right, front, or rear, mentioned in the following embodiments are only for referring to the directions of the drawings. Accordingly, the directional terms used are illustrative and not limiting of the disclosure.

FIG. 1 is a schematic diagram of a near-eye display device according to an embodiment of the disclosure. As shown in FIG. 1, a near-eye display device 100 is disposed in front of an eye 50 of a user. The near-eye display device 100 includes a display 110, a processor 120, a lens array 130, at least one lens 140 (multiple lenses 140 are taken as an example in FIG. 1), a storage element 150, and an operation interface 160.

The display 110 is configured to emit an image beam 112. According to some embodiments, the display 110 is, for example, an organic light emitting diode display, a liquid crystal display, a micro light emitting diode display, or other suitable displays, but not limited thereto.

The processor 120 is coupled to the display 110 and is configured to change a display image 60, so as to perform a short-distance vision examination and a long-distance vision examination on the eye 50. Vision examination data of the user is obtained according to results of the short-distance vision examination and the long-distance vision examination, and the vision examination data is stored, and system parameters, such as a lens position, a lens focal length, and an imaging position, of the near-eye display device 100 are adjusted according to the vision examination data, but not limited thereto. According to some embodiments, the processor 120 is, for example, a central processing unit (CPU), a microprocessor, a digital signal processor (DSP), a programmable controller, or a programmable logic device (PLD), other similar devices, or a combination of the devices, which is not limited in the disclosure. Furthermore, in some embodiments, each function of the processor 120 may be implemented as multiple codes. The codes are stored in a memory and are executed by the processor 120. Alternatively, in some embodiments, each function of the processor 120 may be implemented as one or more circuits. The disclosure does not limit the implementation of each function of the processor 120 by means of software or hardware.

The lens array 130 is disposed on a transmission path of the image beam 112 and is located between the display 110 and the eye 50. In some embodiments, the lens array 130 is a microlens array, but not limited thereto.

The at least one lens 140 is disposed on the transmission path of the image beam 112 and is located between the display 110 and the eye 50. An optical axis of the lens 140 is an optical axis A. In the embodiment, the lenses 140 include a first lens 142 and a second lens 144, wherein the lens array 130 is disposed between the first lens 142 and the second lens 144, and the first lens 142 is disposed between the display 110 and the lens array 130. The image beam 112 is projected to the eye 50 through a pupil 52 via the lens array 130 and the at least one lens 140, so as to form a display image 60.

The storage element 150 is configured to store the vision examination data, wherein the processor 120 is further configured to read the vision examination data from the storage element 150. According to some embodiments, the storage element 150 is, for example, a flash memory, a random access memory, a read only memory, a hard disk, an optical disk, or other suitable memories or storages.

The operation interface 160 is configured to allow the user to input the vision examination data to the near-eye display device 100 through the operation interface 160, and to load the vision examination data through the operation interface 160, so as to adjust system parameters of the near-eye display device 100 according to the vision examination data. According to some embodiments, the operation interface may be a physical button or other devices with similar functions, but the disclosure is not limited thereto.

For the user experience of extended reality, the most important thing is short-distance interaction. Therefore, for the correction of relatively long distances, the framework is mainly based on the ability to complete the correction of vision at short distances. However, the adjustment of a long-distance image cannot degrade the quality of a corrected short-distance image. Therefore, the adjustment of the long-distance image is to fine tune based on the adjustment of the short-distance image. Therefore, in terms of the process, once the user can achieve successful binocular fusion, the exam will be stopped, which means that the near-eye display device can be used normally. The vision examination is divided into two distance tests, which are respectively short distance and long distance. The two types of distances respectively include at least three exam items, vision check, adjustment amplitude check, and eye position check. If there is any abnormal value in each sub-item of the exam, correction will be performed, and a binocular fusion test will be performed after the correction. The detailed usage and examining manners are described below.

Figure 2:
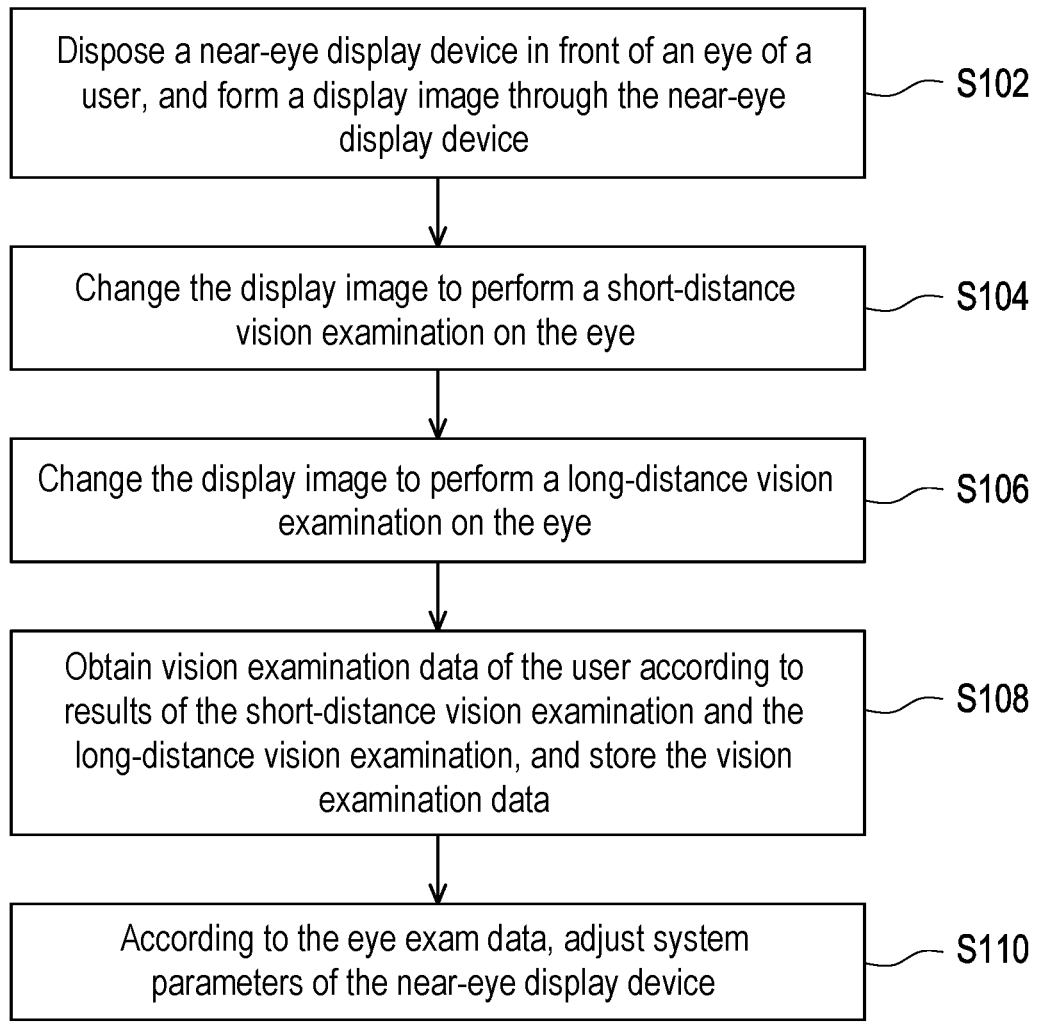
FIG. 2 is a flowchart of a method for operating a near-eye display device according to an embodiment of the disclosure.

FIG. 2 is a flowchart of a method for operating a near-eye display device according to an embodiment of the disclosure. In order to allow the user to have a better user experience when using the near-eye display device, before using the near-eye display device, it is necessary to measure visual parameters of the user. Through the vision examination data of the user, the system parameters of the near-eye display device may be adjusted, so that the user can view a clear image through the near-eye display device.

Please refer to FIG. 1 and FIG. 2. In the embodiment, the method for operating the near-eye display device 100 includes the following steps.

In Step S102, the near-eye display device 100 is disposed in front of the eye 50 of the user, and the display image 60 is formed through the near-eye display device 100. In the step, the processor 120 controls the display 110 to emit the image beam 112, and the display image 60 is formed via the lens array 130 and the at least one lens 140.

In Step S104, the display image 60 is changed to perform the short-distance vision examination on the eye 50. In the step, the processor 120 controls the display 110 to change the display image, so as to perform the short-distance vision examination on the eyes of the user. The detailed steps for the short-distance vision examination will be described below.

In Step S106, the display image 60 is changed to perform the long-distance vision examination on the eye 50. In the step, the processor 120 controls the display 110 to change the display image, so as to perform the long-distance vision examination on the eyes of the user. The detailed steps for the long-distance vision examination will be described below.

In Step S108, the vision examination data of the user is obtained according to the results of the short-distance vision examination and the long-distance vision examination, and the vision examination data is stored. In the step, the user stores the obtained vision examination data of the user in the storage element 150 through the operation interface 160 by the processor 120.

In Step S110, according to the vision examination data, the system parameters of the near-eye display device 100 are adjusted. In the step, the processor adjusts the system parameters, such as a lens position, a lens focal length, and an imaging position, of the near-eye display device 100 by the vision examination data of the user stored in the storage element 150, but not limited thereto.

Figure 3:
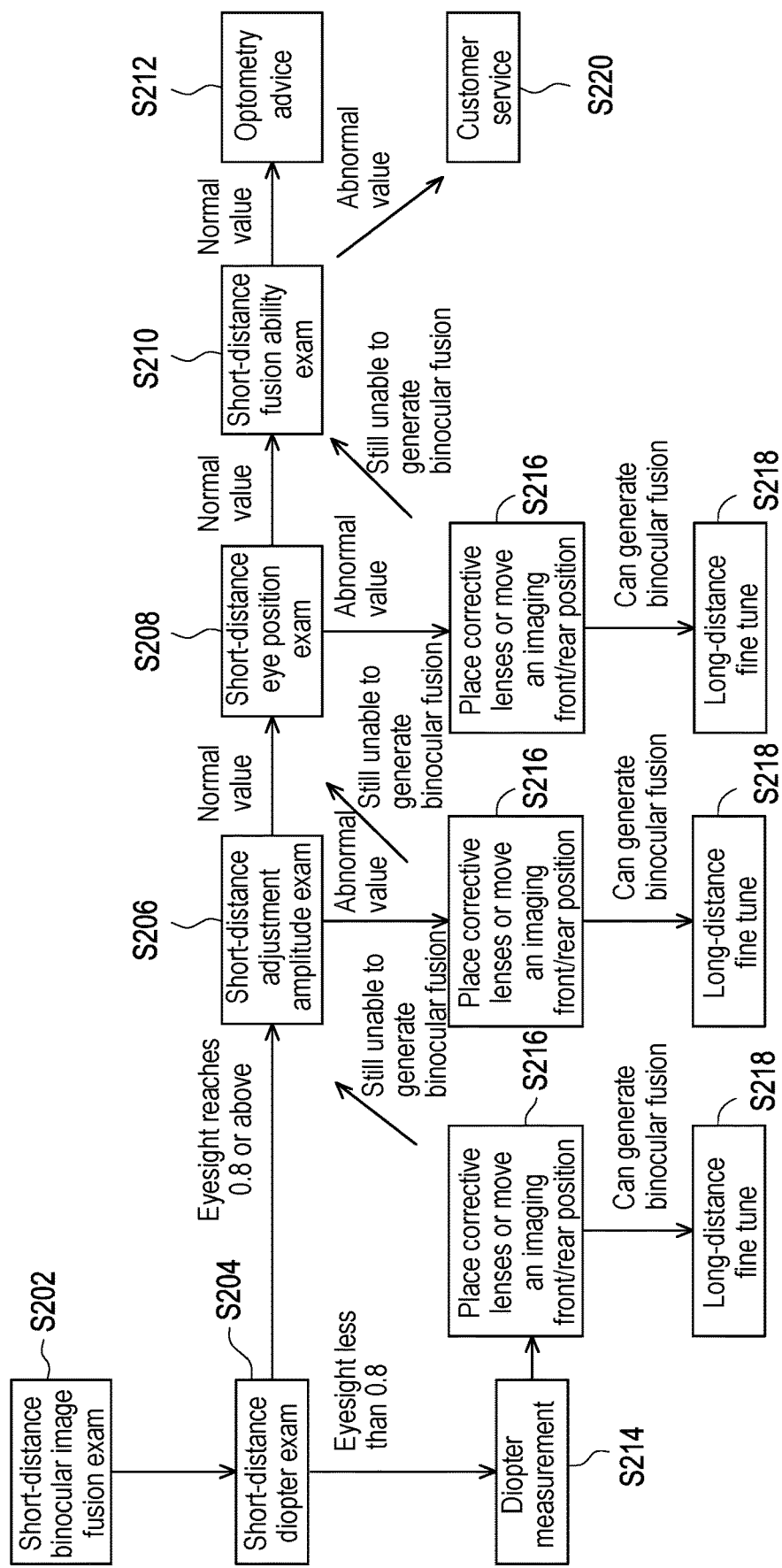
FIG. 3 is a flowchart of a short-distance vision examination according to an embodiment of the disclosure.

FIG. 3 is a flowchart of a short-distance vision examination according to an embodiment of the disclosure. In Step S104 of FIG. 2, the display image 60 is changed to perform the short-distance vision examination on the eye 50. The process of the short-distance vision examination is as shown in FIG. 3, which includes a first short-distance binocular image fusion exam of Step S202, a short-distance diopter exam of Step S204, a short-distance adjustment amplitude exam of Step S206, a short-distance eye position exam of Step S208, and a second short-distance binocular image fusion exam of Step S210.

In Step S202, the user performs the short-distance binocular image fusion exam. The step is used to examine whether both eyes of the user have normal fusion ability when the user is at a short distance, that is, when an image is at a distance of 40 cm from the eyes. The examining process is as shown in FIG. 5.

Figure 5:
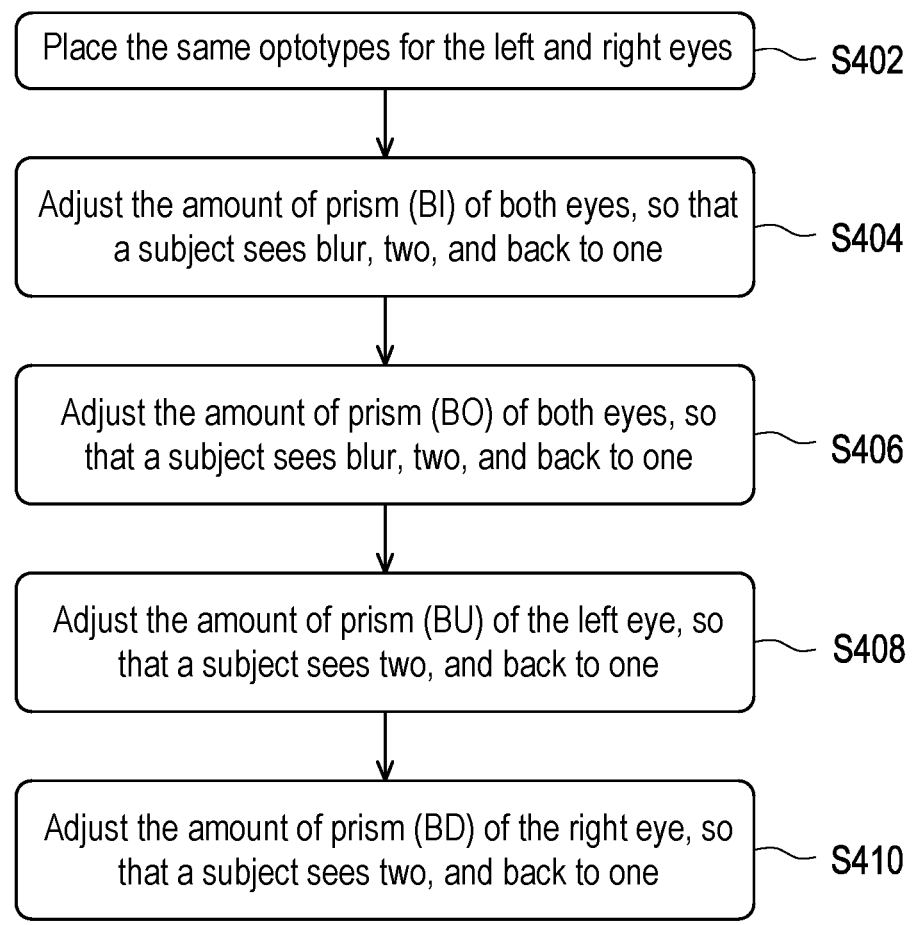
FIG. 5 is a flowchart of a fusion ability exam according to an embodiment of the disclosure.

FIG. 5 is a flowchart of a fusion ability exam according to an embodiment of the disclosure. In Step S402 of FIG. 5, the display image 60 is first presented to the left and right eyes. The display image 60 includes multiple optotypes. In the embodiment, the number of optotypes is two, which respectively correspond to the left eye and the right eye. The positions of the optotypes are set at a distance of 40 cm from the eye 50. The near-eye display device 100 projects the display image 60 to the eye 50.

In Step S404, the amount of prism of both eyes is adjusted to be base in (BI), so that the optotypes seen by the left and right eyes of the user at the same time sequentially become blurred images, become two optotypes, and then back to being one optotype, that is, the two optotypes are fused into a single optotype. The step is performed once, and the corresponding amount of prism BI is recorded.

In Step S406, the amount of prism of both eyes is adjusted to be base out (BO), so that the optotypes seen by the left and right eyes of the user at the same time sequentially become blurred images, become two optotypes, and then back to being one optotype, that is, the two optotypes are fused into a single optotype. The step is performed once in total, and the corresponding amount of prism BO is recorded.

In Step S408, the amount of prism of the left eye is adjusted to be base up (BU), so that the optotypes seen by the left and right eyes of the user at the same time sequentially become two optotypes, and then back to being one optotype, that is, the two optotypes are fused into a single optotype. The step is performed once in total, and the corresponding amount of prism BU is recorded.

In Step S410, the amount of prism of the right eye is adjusted to be base down (BD), so that the optotypes seen by the left and right eyes of the user at the same time sequentially become two optotypes, and then back to being one optotype, that is, the two optotypes are fused into a single optotype. The step is performed once in total, and the corresponding amount of prism BD is recorded.

According to an exam result of Step S202, if the user can generate binocular fusion, the long-distance vision examination of Step S218 is performed. If binocular fusion is not generated in any one of Steps S404, S406, S408, and S410, the short-distance diopter exam of Step S204 is performed.

In Step S204, the user performs the short-distance diopter exam. The step is used to examine whether the user can clearly see the optotype at a short distance, and then measure corresponding visual parameters.

Figures 6, 7:
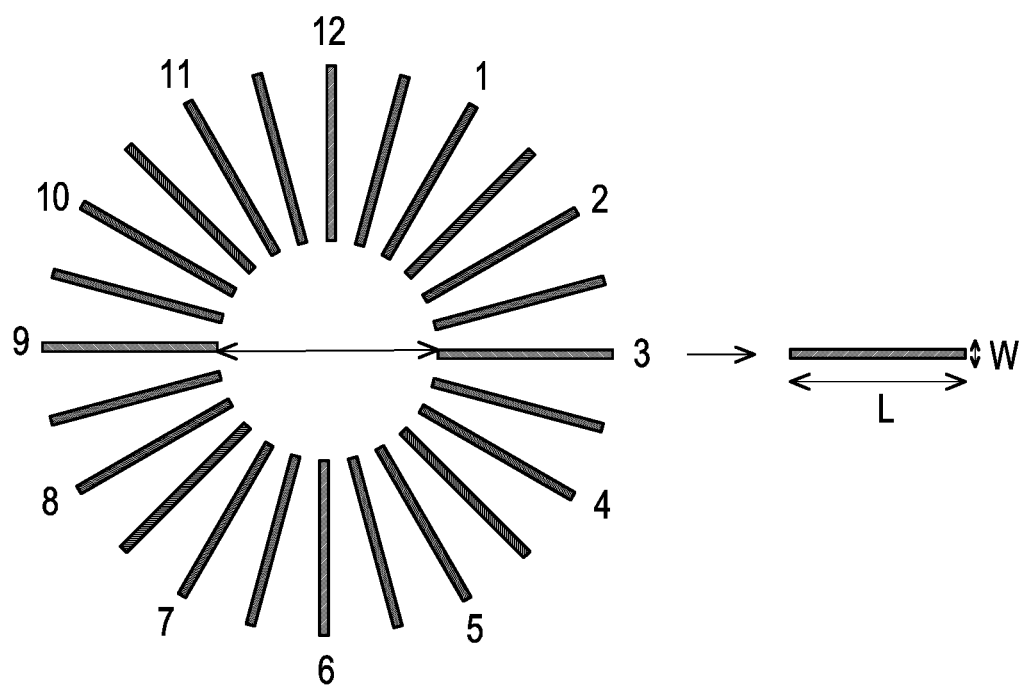
FIG. 6 is a schematic diagram of a vision examination optotype table according to an embodiment of the disclosure.
FIG. 7 is a schematic diagram of an optotype and clock dial chart for a diopter exam according to an embodiment of the disclosure.

In Step S204, the display image 60 includes multiple optotypes, the positions of the optotypes are set at a distance of 40 cm from the eye 50, and the display image 60 is projected to the eye 50. FIG. 6 is a schematic diagram of a vision examination optotype table according to an embodiment of the disclosure. In a short-distance vision measurement, the relationship between visual conditions and optotype sizes is as shown in Table 1. In FIG. 6, the optotypes used for a vision examination respectively correspond to the vision of Snellen scores 20/30, 20/25, and 20/20 in the Snellen visual acuity (VA) system or correspond to the vision of 0.7, 0.8, and 1.0 from large to small. The optotype size that can be clearly seen by the user is used as the optotype size basis for subsequent exams.

TABLE 1

Relationship between short-distance visual conditions and optotype sizes

| VA | Optotype size (located at 40 cm) | Line thickness (located at 40 cm) |
| --- | --- | --- |
| 20/30 | 0.09 cm | 0.018 cm |
| 20/25 | 0.07 cm | 0.014 cm |
| 20/20 | 0.06 cm | 0.012 cm |

In the short-distance vision measurement, if the vision of the eye 50 is greater than or equal to 0.8, the short-distance adjustment amplitude exam of Step S206 is performed. If the vision of the eye 50 is less than 0.8, the diopter exam of Step S214 is performed on the eye 50 to measure the spherical aberration and the astigmatism of the eye 50, and corrective lenses are placed or the front/rear position of the display image 60 is changed according to a vision measurement result and a result of the diopter exam, so that the vision of the eye 50 is greater than or equal to 0.8.

Figure 8:
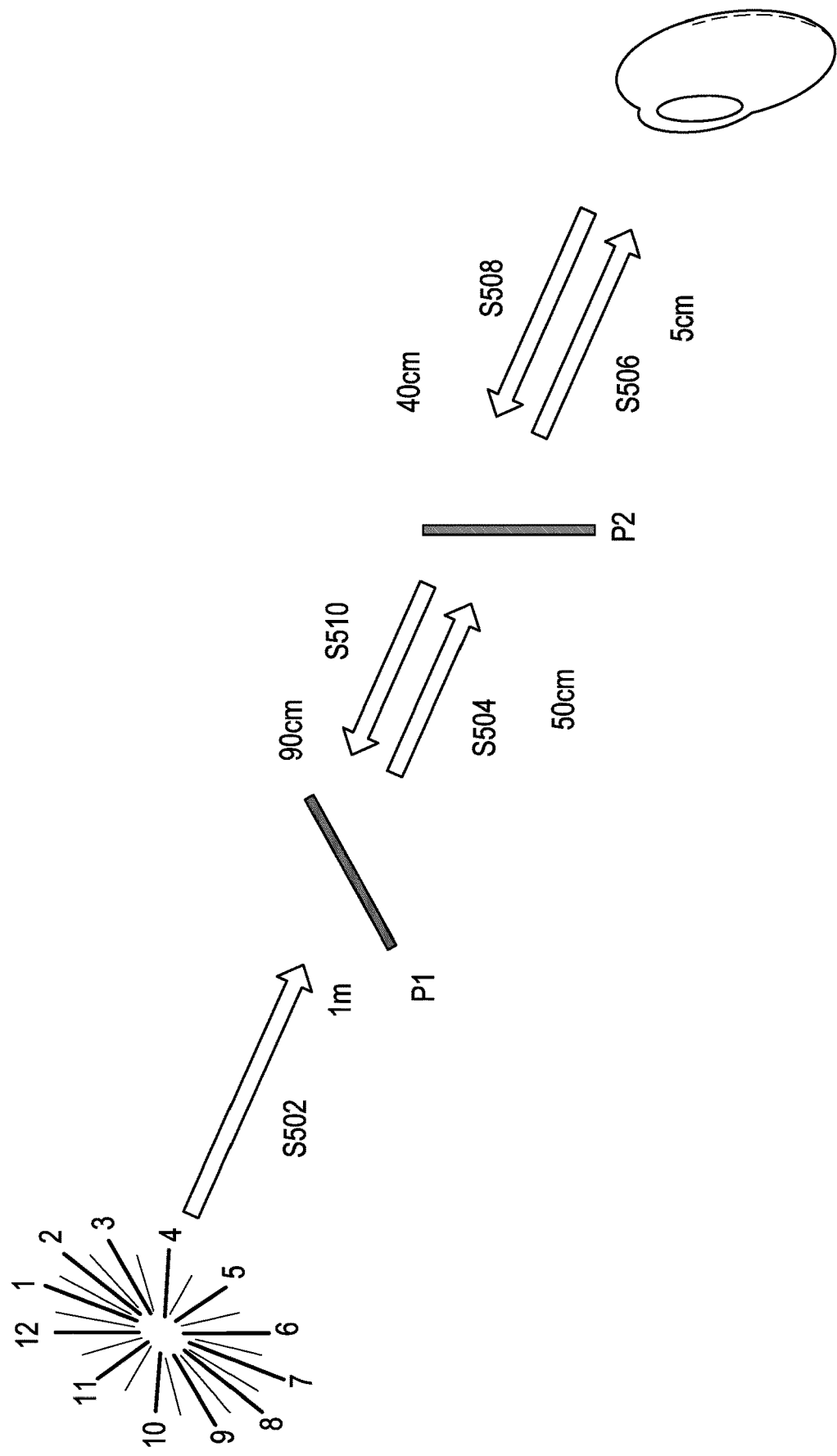
FIG. 8 is a schematic diagram of a method for examining diopter according to an embodiment of the disclosure.

In Step S214, the user performs a diopter measurement. FIG. 7 is a schematic diagram of an optotype and clock dial chart for a diopter exam according to an embodiment of the disclosure. FIG. 8 is a schematic diagram of a method for examining diopter according to an embodiment of the disclosure.

Please refer to FIG. 7 and FIG. 8 at the same time. In a short-distance diopter measurement, a display image with the optotype shown in FIG. 7 is placed at a distance of 40 cm from the eyes, and the optotype is moved in the order of numbers 1 to 5 in FIG. 8. The optotype of FIG. 7 is a bell diagram with 12 scales from 1 to 12. Each scale has a corresponding line segment. As shown in FIG. 7, a length L of a black line segment is 9 cm, a width w of the black line segment is 0.3 cm, and a diameter D of a central circle is 6.2 cm.

In Step S502, the position of a display image is controlled by a system to start moving closer from 1 m, and the user observes a position when one line of the clock dial chart changes from blur to clear. The position is a first focal plane P1.

In Step S504, the display image continues to be moved closer, and the user is informed to pay attention to the sharpness of a line segment in the normal direction of the line segment that is clear in the first focal plane. For example, if in the first focal plane P1, the clear line segment seen by the user is a horizontal line segment, that is, along the direction 3-9 of the clock dial chart of FIG. 7, in Step S504, the sharpness of a vertical line segment in the direction 6-12 needs to be observed, so as to be used as a clear line segment for judging a second focal plane. When the position of the second focal plane is clear, the position of the display image is recorded as the position of a second focal plane P2.

In Step S506, the display image continues to be moved closer until the entire optotype is clear in all directions.

In Step S508, the display image is moved farther in the opposite direction, and the position of the second focal plane P2 is recorded again (confirmed twice).

In Step S510, the display image continues to be moved farther in the opposite direction, and the position of the first focal plane P1 is recorded again (confirmed twice).

After obtaining the positions of the first focal plane P1 and the second focal plane P2 according to the above steps, the spherical aberration and the astigmatism of the user may be obtained. The spherical aberration is an average of the first focal plane and the second focal plane, and the astigmatism is a difference value between the first focal plane and the second focal plane. The units of the spherical aberration and the astigmatism are both diopters (D).

If the positions of the first focal plane P1 and the second focal plane P2 are the same, for example, it is impossible to distinguish which line segment is clear, and the line segments in various directions appear to be all clear or all blurred, it means that the user has only spherical aberration and no astigmatism.

After the diopter measurement is performed in Step S214, the spherical aberration and the astigmatism of the eyes of the user corresponding to a short distance may be obtained.

In Step S216, the corrective lenses are placed in the near-eye display device 100 or the imaging front/rear position is moved, so that the vision of the user reaches 0.8 or more. The corrective lenses may be placed by, for example, adding an additional lens to the lens 140 of the near-eye display device 100 or changing the focal length of the lens array 130 and the lens 140, so as to adjust the imaging position of the display image 60, so that the vision of the eye 50 is greater than or equal to 0.8.

After placing the corrective lenses or changing the position of the display image 60, so that the vision of the eye 50 is greater than or equal to 0.8, if the user may generate binocular fusion, the long-distance vision examination of Step S218 is performed. If the user still cannot generate binocular fusion, the short-distance adjustment amplitude exam of Step S206 is performed.

In Step S206, the user performs the short-distance adjustment amplitude exam. The short-distance adjustment amplitude exam may be used to examine the closest visible focus distance of the user, that is, the short-distance adjustment power of the eyes of the user.

Figure 9:
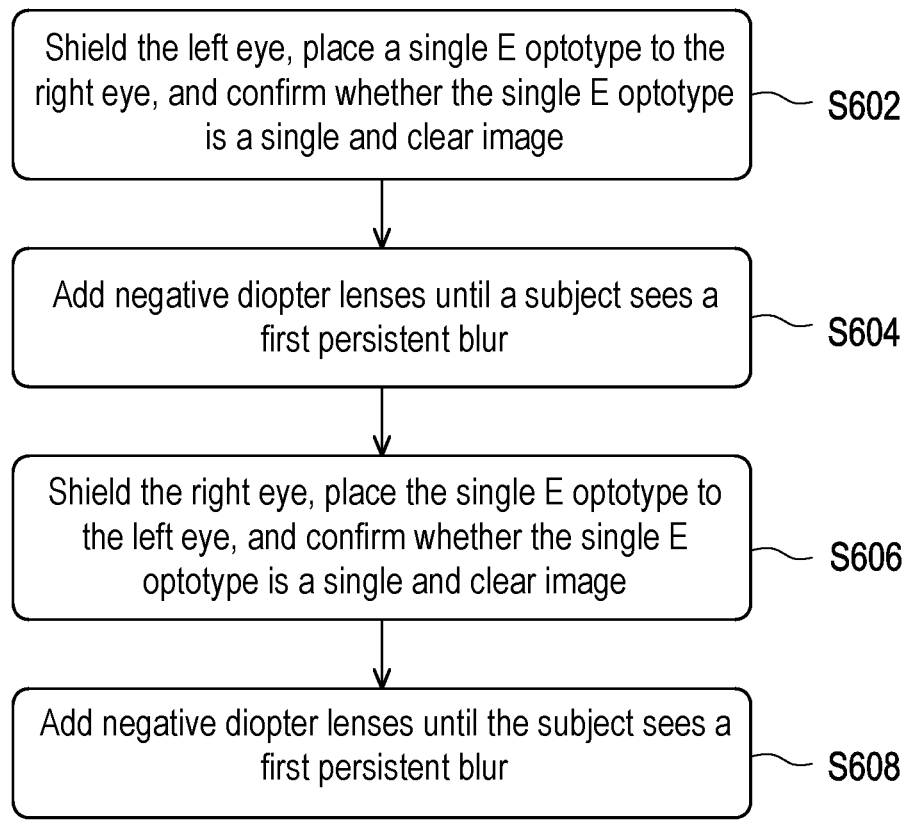
FIG. 9 is a flowchart of a short-distance adjustment amplitude exam according to an embodiment of the disclosure.

FIG. 9 is a flowchart of a short-distance adjustment amplitude exam according to an embodiment of the disclosure. The step of the short-distance adjustment amplitude exam includes projecting the display image 60 to the eye 50, so as to examine the closest visible focus distance of the eye 50 of the user. The specific implementation method is as follows.

In Step S602, the near-eye display device 100 first shields the left eye, and presents the display image 60 with a single E optotype to the right eye. The user confirms whether the single E optotype is a single and clear image.

In Step S604, negative diopter lenses continue to be added until the right eye of the user sees a first persistent blur. The value plus +2.50 D is the adjustment amplitude of the right eye. The test is performed once in total.

In Step S606, the near-eye display device 100 shields the right eye, and presents the display image 60 with the single E optotype to the left eye. The user confirms whether the single E optotype is a single and clear image.

In Step S608, negative diopter lenses continue to be added until the right eye of the user sees the first persistent blur. The value plus +2.50 D is the adjustment amplitude of the left eye. The test is performed once in total.

According to a short-distance adjustment amplitude exam result of Step S206, if the closest visible focus distance is a normal value, the short-distance eye position exam of Step S206 continues to be performed. If the closest visible focus distance is an abnormal value, Step S216 is proceeded to place the corrective lenses or change the front/rear position of the display image 60, so that the closest visible focus distance is a normal value. After placing the corrective lenses or changing the position of the display image 60, so that the closest visible focus distance is a normal value, if binocular fusion may be generated, the long-distance vision examination of Step S218 is performed. If binocular fusion is not generated, the short-distance eye position exam of Step S206 is performed.

Table 2 is a Donder's table, indicating that the adjustment amplitude (the reciprocal of the closest visible focus distance) is related to age. The normal value of the closest visible focus distance is the reciprocal of the adjustment amplitude, and the range is plus or minus 10%. If the closest visible focus distance exceeds the range, the closest visible focus distance is an abnormal value.

TABLE 2

Donder's table

| Age (y.o.) | Adjustment amplitude (D) |
|---|---|
| 10 | 14.00 |
| 15 | 12.00 |
| 20 | 10.00 |
| 25 | 8.50 |
| 30 | 7.00 |
| 35 | 5.50 |
| 40 | 5.00 |
| 45 | 3.50 |
| 50 | 2.50 |
| 55 | 1.75 |
| 60 | 1.00 |
| 65 | 0.50 |
| 70 | 0.25 |
| 75 | 0.00 |

In Step S208, the user performs the short-distance eye position exam to obtain short-distance horizontal and vertical eye position information of the user.

Figure 10:
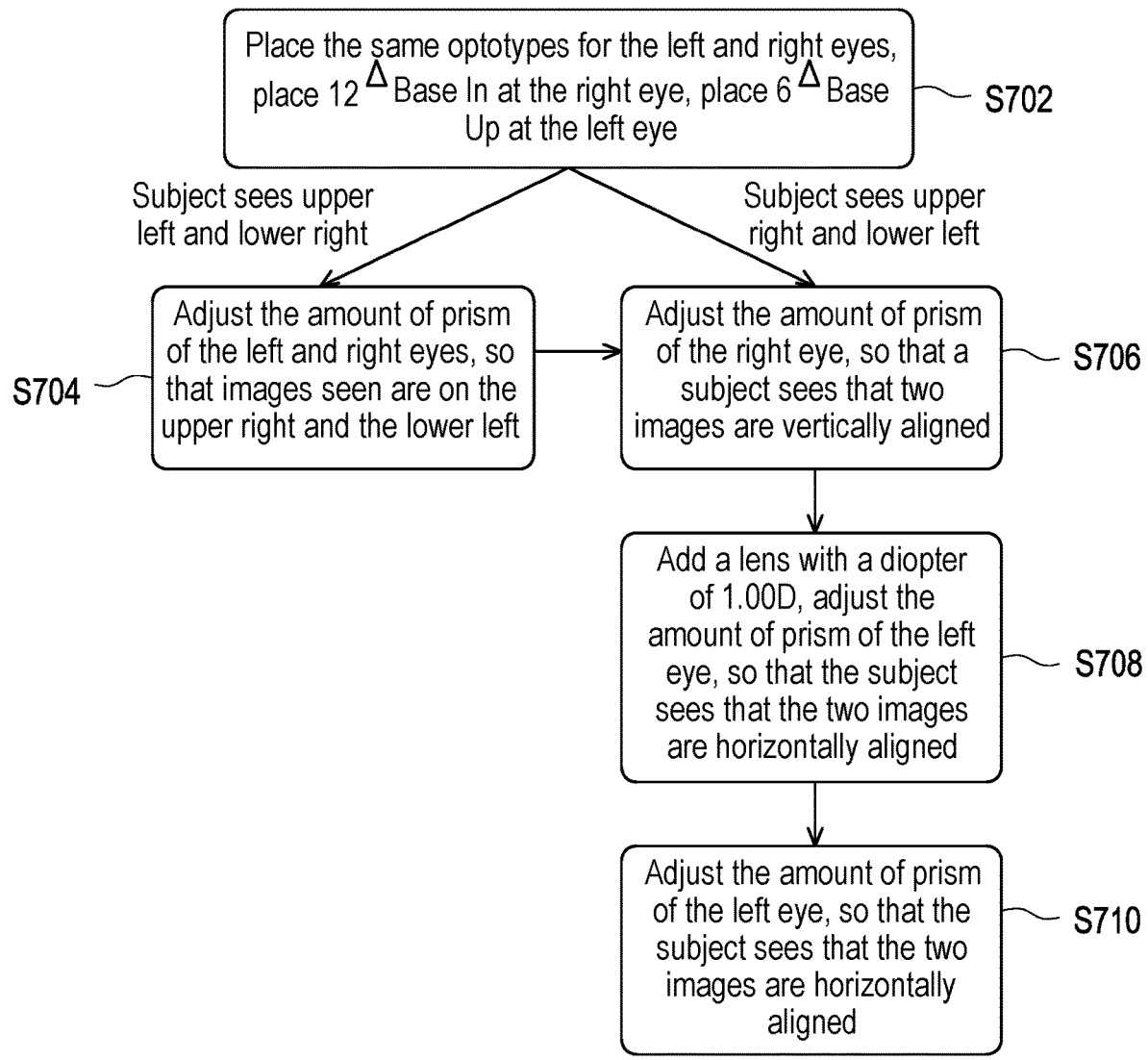
FIG. 10 is a flowchart of a short-distance eye position exam according to an embodiment of the disclosure.

FIG. 10 is a flowchart of a short-distance eye position exam according to an embodiment of the disclosure. The step of the short-distance eye position exam includes projecting the display image 60 to the eye 50, so as to examine the short-distance horizontal eye position information and the short-distance vertical eye position information of the user. The specific implementation method is as follows.

In Step S702, the same optotypes are placed for the left and right eyes. The optotype corresponding to the right eye is placed at the position of 12 $^\triangle$Base In, and the optotype corresponding to the left eye is placed at the position of 6 $^\triangle$Base Up. The degree of prism $^\triangle$Base In is horizontally inward (both eyes are facing the nose), and $^\triangle$Base Up is a vertically upward adjustment. The near-eye display device 100 performs corresponding image translation according to the field of view of the user, so as to achieve the effect of the required degree of prism. When the optotype corresponding to the right eye is placed at the position of 12 $^\triangle$Base In, and the optotype corresponding to the left eye is placed at the position of 6 $^\triangle$Base Up, if the user sees that the two optotypes are respectively on the upper left and the lower right, Step S704 is performed. If the user sees that the two optotypes are respectively on the upper right and the lower left, Step S706 is performed.

In Step S704, after adjusting the amount of prism of the left and right eyes, so that the positions of the two optotypes seen by the left and right eyes are on the upper right and the lower left, Step S706 is performed.

In Step S706, the amount of prism of the right eye is adjusted to change the vertical height of the optotype seen by the right eye, so that the user can see that the two optotypes are vertically aligned. When the two optotypes are vertically aligned, the value is a horizontal eye position amount. The step is tested once in total. Step S708 is then performed.

In Step S708, a lens with a diopter of 1.00 D is added to stimulate eye adjustment by the negative diopter lens. After adding the lens, the amount of prism of the left eye is adjusted, so that the user can see that the two optotypes are horizontally aligned. When the two optotypes are horizontally aligned, the value is an AC/A ratio of accommodative convergence (AC) to accommodation (A). The step is tested once in total. Step S710 is then performed.

In Step S710, the lens with the diopter of 1.00 D added in Step S708 is removed, and the amount of prism of the left eye is adjusted to change the horizontal level of the optotype seen by the left eye, so that the user can see that the two optotypes are horizontally aligned. When the two optotypes are horizontally aligned, the value is a vertical eye position amount. The step is tested once in total.

In Step S208, if the short-distance horizontal eye position information and the short-distance vertical eye position information are normal values, the second short-distance binocular image fusion exam of Step S210 is performed. If the short-distance horizontal eye position information or the short-distance vertical eye position information is an abnormal value, Step S216 is performed to place the corrective lenses or change the front/rear position of the display image 60, so that the short-distance horizontal eye position information and the short-distance vertical eye position information are adjusted to normal values. The normal value of the short-distance (40 cm) eye position information (including the short-distance horizontal eye position information and the short-distance vertical eye position information) is exophoria $3^\Delta$, and the standard deviation is $+/-3^\Delta$. The short-distance eye position information outside the range is considered to be an abnormal value. After performing Step S216 to change the position of the display image 60, so that the short-distance horizontal eye position information and the short-distance vertical eye position information are normal values, if binocular fusion may be generated, the long-distance vision examination of Step S218 is performed. If binocular fusion is not generated, the second short-distance binocular image fusion exam of Step S210 is performed.

In Step S210, the user performs a short-distance fusion ability exam. In the exam, the near-eye display device 100 respectively forms different images for the left and right eyes to examine whether the user can fuse the two different images into a single image. The short-distance fusion ability of the user includes short-distance vertical fixation disparity and short-distance horizontal fixation disparity. The fixation disparity (FD) refers to the condition that when both eyes are fixated on an object, the image does not actually stimulate the corresponding points of the retinas of both eyes, but still falls within Panum's fusion area. Thus, the presence of the fixation disparity indicates that in the case of binocular vision, there is a slight hyperconvergence (esotropic fixation disparity) or insufficient convergence (exotropic fixation disparity) of the lines of sight of both eyes.

Figure 12:
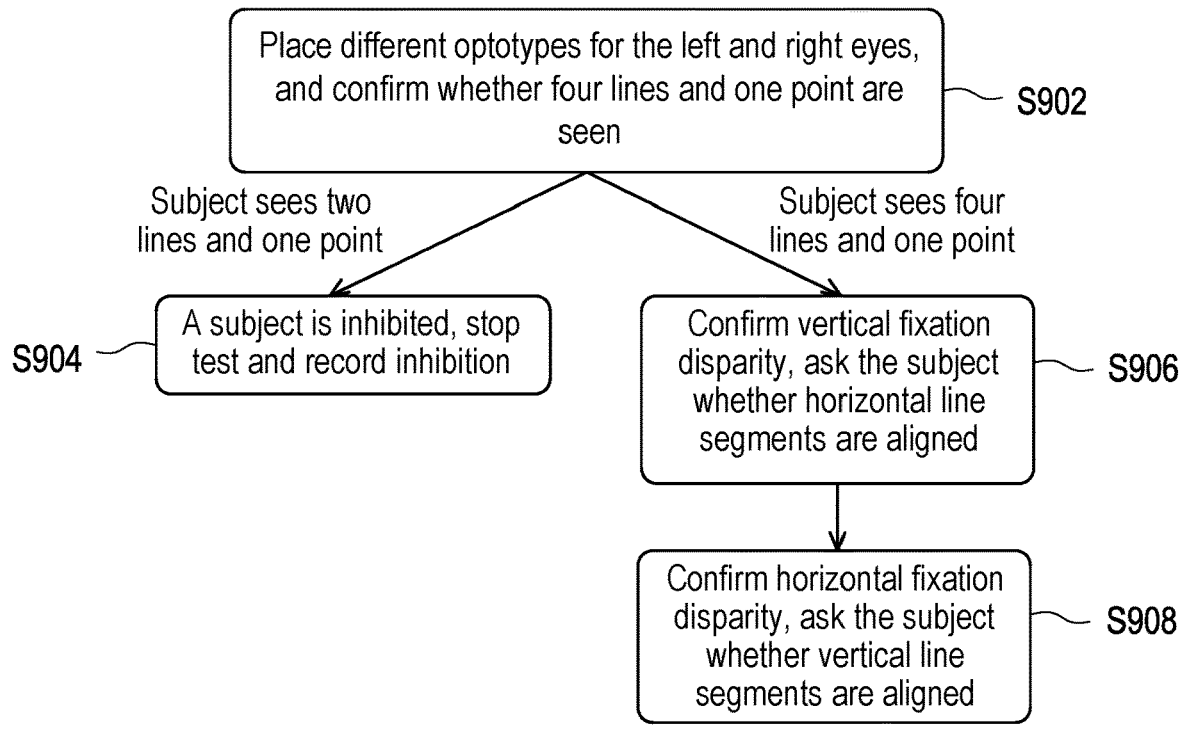
FIG. 12 is a flowchart of a fixation disparity exam according to an embodiment of the disclosure.
Figure 13A:
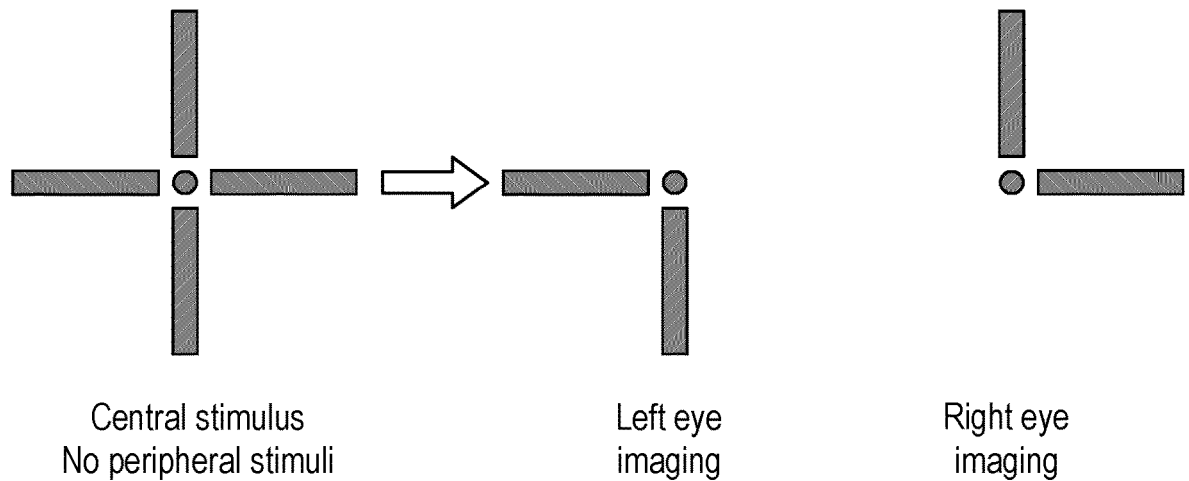
FIG. 13A and FIG. 13B are schematic diagrams of a fixation disparity exam according to an embodiment of the disclosure.
Figure 13B:
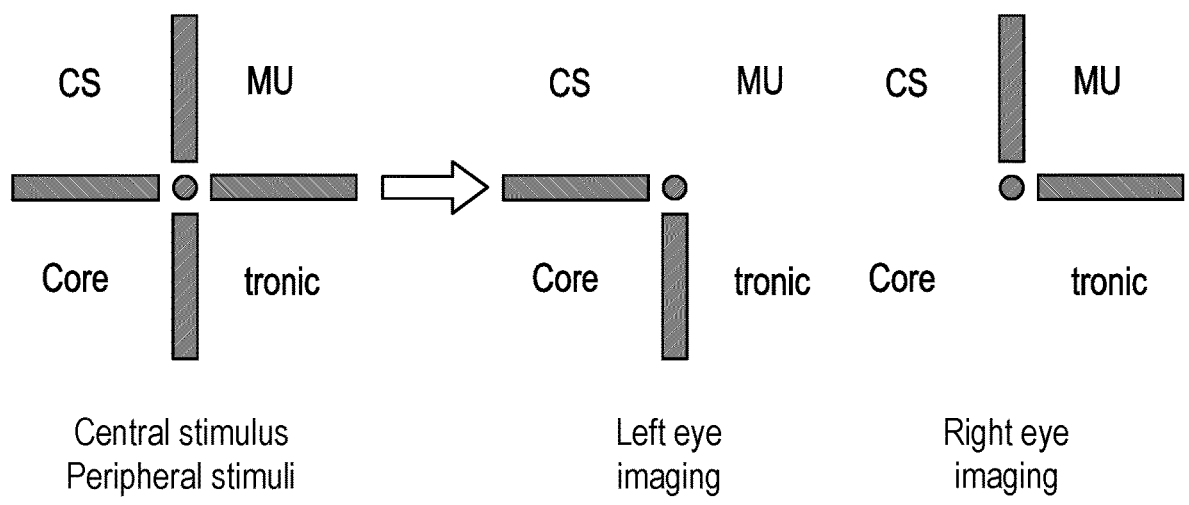

FIG. 12 is a flowchart of a fixation disparity exam according to an embodiment of the disclosure. FIG. 13A and FIG. 13B are schematic diagrams of a fixation disparity exam according to an embodiment of the disclosure. FIG. 13A and FIG. 13B show two different types of optotypes. In FIG. 13A, the optotype consists of one point and four straight lines. The left eye imaging corresponding to the optotype includes a pattern formed by a point in the middle and two straight lines on the left and below. The right eye imaging corresponding to the optotype includes a pattern formed by the point in the middle and two straight lines on the right and above. At this time, the image has a central stimulus and no peripheral stimuli. When the left and right eyes generate correct fusion, a complete pattern as shown on the left of FIG. 13A may be obtained. The pattern of FIG. 13B is similar to that of FIG. 13A, except that there are other patterns of peripheral stimuli around the pattern of FIG. 13B. For example, in FIG. 13B, there are words such as "CS", "MU", "Core", and "tronic", but the stimuli are not limited thereto.

The second short-distance binocular image fusion exam of Step S210 includes setting the positions of multiple optotypes at a distance of 40 cm from the eye 50 to project the display image 60 to the eye 50. The display image 60 includes multiple optotypes. The specific implementation method is as follows.

In Step S902, the near-eye display device 100 respectively displays different optotypes for the left and right eyes, as shown in FIG. 13A or FIG. 13B, and whether four lines and one point are seen is confirmed.

In Step S902, if the user sees only two lines and one point, Step S904 is performed. If the user sees four lines and one point, Step S906 is performed.

In Step S904, the user is inhibited, so only two lines and one point are seen. When the situation happens, the test is stopped and the inhibition of the user is recorded.

In Step S906, the vertical fixation disparity is confirmed, and the user is asked whether horizontal line segments of images of the left and right eyes are aligned. If aligned, Step S908 is performed.

In Step S908, the horizontal fixation disparity is confirmed, and the user is asked whether vertical line segments of the images of the left and right eyes are aligned.

In Step S210, if the short-distance fusion ability, that is, the short-distance vertical fixation disparity and the short-distance horizontal fixation disparity, are both normal values, is performed Step S212 to seek optometry advice. If both the short-distance vertical fixation disparity and the short-distance horizontal fixation disparity are abnormal values, Step S220 is performed to seek customer service, and the exam is stopped. The units of the short-distance vertical fixation disparity and the short-distance horizontal fixation disparity are expressed in the degree of prism, and the normal value is less than 0.254. Any value greater than 0.254 is an abnormal value.

In Step S212, as shown in the short-distance vision examination of FIG. 3, at this time, the short-distance diopter, the short-distance adjustment amplitude, and the short-distance eye position of the user are all normal. Therefore, in the case where the visual parameters are all normal, but both eyes are still unable to generate normal fusion, at this time, the exam should be stopped, and the assistance of an ophthalmologist should be sought to provide appropriate optometry advice.

In Step S220, when the short-distance vertical fixation disparity and the short-distance horizontal fixation disparity are both abnormal values, it means that the near-eye display device 100 cannot correct the visual condition of the user. Therefore, customer service needs to be sought to resolve the issue.

After the short-distance vision examination as shown in FIG. 3 is completed, the short-distance vision examination data, including the diopter, the astigmatism, the eye position, and a combination thereof, of the user may be obtained.

Figure 4:
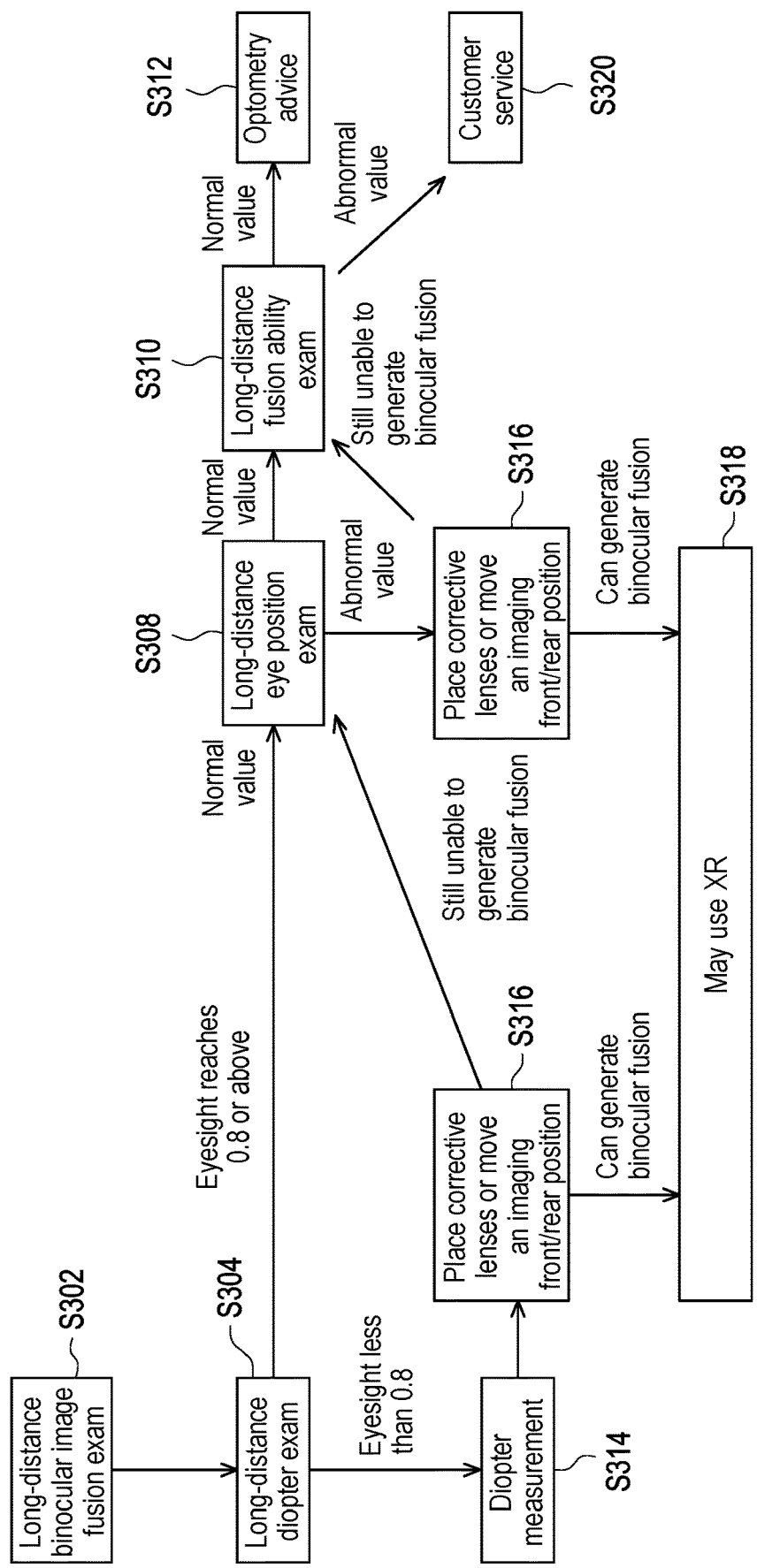
FIG. 4 is a flowchart of a long-distance vision examination according to an embodiment of the disclosure.

In the flowchart of FIG. 3, when a long-distance fine tuning of Step S218 is executed, that is, the long-distance vision examination is performed according to the flowchart of long-distance vision examination shown in FIG. 4, that is, Step S106 of FIG. 2 is executed.

FIG. 4 is a flowchart of a long-distance vision examination according to an embodiment of the disclosure. In Step S106 of FIG. 2, the display image 60 is changed to perform the long-distance vision examination on the eye 50. The process of the long-distance vision examination is as shown in FIG. 4 and includes a first long-distance binocular image fusion exam of Step S302; a long-distance diopter exam of Step S304; a long-distance eye position exam of Step S308; and a second long-distance binocular image fusion exam of Step S310.

In Step S302, the user performs the long-distance binocular image fusion exam. The step is used to examine whether both eyes of the user have normal fusion ability when the user is at a long distance, that is, when an image is at a distance of 6 meters from the eyes. The examining process is as shown in FIG. 5.

When performing the long-distance binocular image fusion exam of Step S302, the examining manner is the same as that of the short-distance binocular image fusion exam of Step S202, so there is no repetition. The difference is that during the short-distance binocular image fusion exam of Step S202, the image position is set at a distance of 40 cm from the eyes, while during the long-distance binocular image fusion exam of Step S302, the image position is set at a distance of 6 meters from the eyes.

According to an exam result of Step S302, if the user may generate binocular fusion, the exam ends, and it is considered that the user can use the near-eye display device 100. If binocular fusion is not generated in any one of Steps S404, S406, S408, and S410, the long-distance diopter exam of Step S304 is performed.

In Step S304, the user performs the long-distance diopter exam. The step is used to examine whether the user can clearly see the optotype located at a long distance, and then measure corresponding visual parameters.

In the long-distance diopter exam of Step S304, the examining manner is the same as that of the short-distance diopter exam of Step S204, so there will be no repetition. The difference is that during the short-distance diopter exam of Step S204, the image position is set at a distance of 40 cm from the eyes, while during the long-distance diopter exam of Step S304, the image position is set at a distance of 6 meters from the eyes.

FIG. 6 is a schematic diagram of a vision examination optotype table according to an embodiment of the disclosure. In a long-distance vision measurement, the relationship between visual conditions and optotype sizes is as shown in Table 3.

TABLE 3

Relationship between long-distance visual conditions and optotype sizes

| VA | Optotype size (located at 6 meters) | Line thickness (located at 6 meters) |
|---|---|---|
| 20/30 | 1.31 cm | 0.262 cm |
| 20/25 | 1.09 cm | 0.218 cm |
| 20/20 | 0.87 cm | 0.174 cm |

In the long-distance vision measurement, if the vision of the eye 50 is greater than or equal to 0.8, the long-distance eye position exam of Step S308 is performed. If the vision of the eye 50 is less than 0.8, the diopter exam of Step S314 is performed on the eye 50 to measure the spherical aberration and the astigmatism of the eye 50, and place the corrective lenses or change the front/rear position of the display image 60 according to a vision measurement result and a result of the diopter exam, so that the vision of the eye 50 is greater than or equal to 0.8.

In Step S314, the user performs the diopter measurement. When performing the diopter measurement of Step S314, the examining manner is the same as that of the diopter measurement of Step S214, so there will be no repetition. The difference is that during the diopter measurement of Step S214, the image position is set at a distance of 40 cm from the eyes, while during the diopter measurement of Step S314, the image position is set at a distance of 6 meters from the eyes.

After performing the diopter measurement of Step S314, the spherical aberration and the astigmatism of the eyes of the user corresponding to a long distance may be obtained.

In Step S316, the corrective lenses are placed in the near-eye display device 100 or the imaging front/rear position is moved, so that the vision of the user reaches 0.8 or more. The corrective lenses may be placed by, for example, adding an additional lens to the lens 140 of the near-eye display device 100 or changing the focal length of the lens array 130 and the lens 140, so as to adjust the imaging position of the display image 60, so that the vision of the eye 50 is greater than or equal to 0.8.

After placing the corrective lenses or changing the position of the display image 60, so that the vision of the eye 50 is greater than or equal to 0.8, if the user may generate binocular fusion, the exam ends, and it is considered that the user may use the near-eye display device 100. If binocular fusion is not generated, the long-distance eye position exam of Step S308 is performed.

Compared with the short-distance vision examination of FIG. 3, the long-distance vision examination of FIG. 4 does not need to perform the exam corresponding to the short-distance adjustment amplitude exam of Step S206 of FIG. 3.

In Step S308, the user performs the long-distance eye position exam to obtain long-distance horizontal and vertical eye position information of the user.

Figure 11:
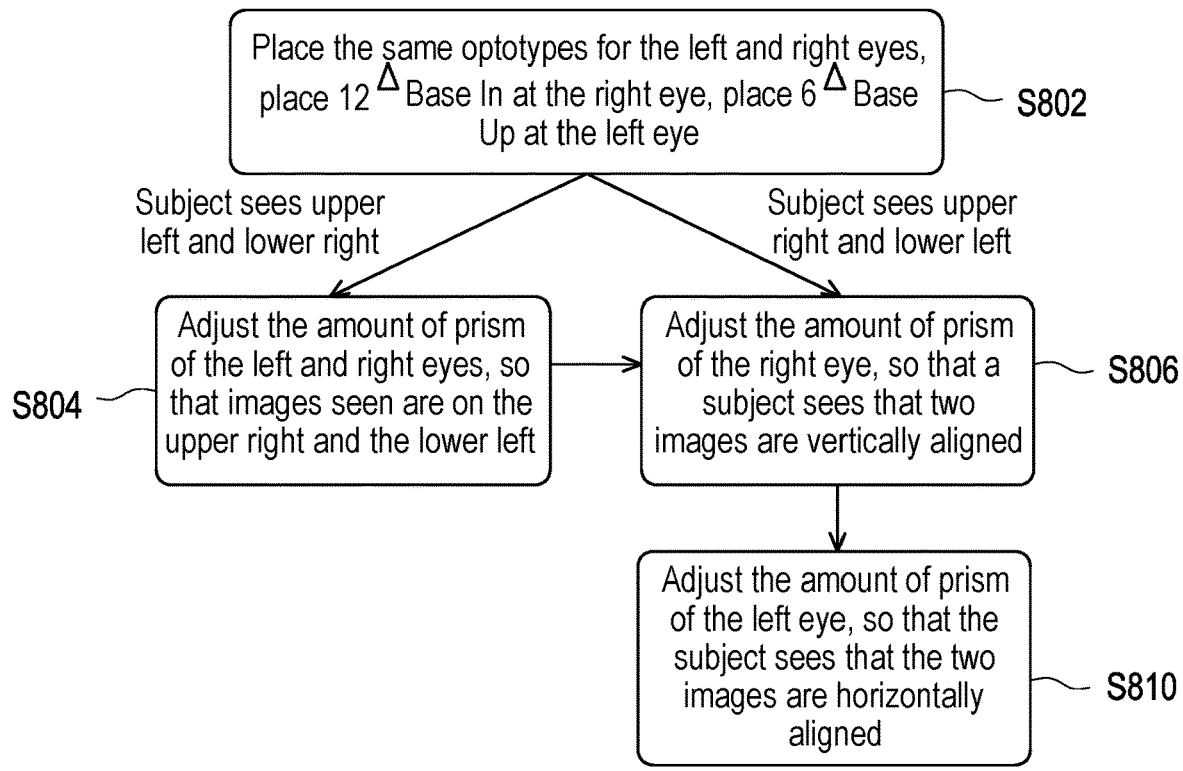
FIG. 11 is a flowchart of a long-distance eye position exam according to an embodiment of the disclosure.

FIG. 11 is a flowchart of a long-distance eye position exam according to an embodiment of the disclosure. The step of the long-distance eye position exam includes projecting the display image 60 to the eye 50, so as to examine the long-distance horizontal eye position information and the long-distance vertical eye position information of the user. The specific implementation method is as follows.

The flowchart of the long-distance eye position exam shown in FIG. 11 has similar steps to the flowchart of the short-distance eye position exam shown in FIG. 10, wherein Steps S802, S804, S806, and S810 of FIG. 11 respectively correspond to Steps S702, S704, S706, and S710 of FIG. 10, and will not be repeated. The difference lies in that in the flowchart of the long-distance eye position exam shown in FIG. 11, after the amount of prism of the right eye is adjusted in Step S806, so that the user can see that the two images are vertically aligned, there is no need to add the lens with the diopter of 1.00 D as shown in Step S708 of FIG. 10, and Step S810 is directly performed to adjust the amount of prism of the left eye, so that the user can see that the two images are horizontally aligned. In other words, in the long-distance eye position exam, the AC/A ratio does not need to be measured.

In Step S308, if the long-distance horizontal eye position information and the long-distance vertical eye position information are normal values, the second long-distance binocular image fusion exam of Step S310 is performed. If the long-distance horizontal eye position information or the long-distance vertical eye position information is an abnormal value, Step S316 is performed to place the corrective lenses or change the front/rear position of the display image 60, so that the long-distance horizontal eye position information and the long-distance vertical eye position information are adjusted to normal values. The normal value of the long-distance (6 meters) eye position information (including the long-distance horizontal eye position information and the long-distance vertical eye position information) is exophoria $1^\Delta$, and the standard deviation is $+/-2^\Delta$. The long-distance eye position information outside the range is considered to be an abnormal value. In Step S316, after changing the position of the display image 60, so that the long-distance horizontal eye position information and the long-distance vertical eye position information are normal values, if the user may generate binocular fusion, the exam ends, and it is considered that the user may use the near-eye display device 100. If binocular fusion is not generated, the second long-distance binocular image fusion exam of Step S310 is performed.

In Step S310, the user performs a long-distance fusion ability exam. In the exam, the near-eye display device 100 respectively forms different images for the left and right eyes to examine whether the user can fuse the two different images into a single image. The long-distance fusion ability of the user includes long-distance vertical fixation disparity and long-distance horizontal fixation disparity.

The step of the second long-distance binocular image fusion exam of Step S310 includes setting the positions of multiple optotypes at a distance of 6 meters from the eye 50 to project the display image 60 to the eye 50. The display image 60 includes multiple optotypes. The specific implementation method is similar to Step S210 of FIG. 3, and will not be repeated.

In Step S310, if the long-distance fusion ability, that is, the long-distance vertical fixation disparity and the long-distance horizontal fixation disparity, are both normal values, Step S312 is performed to seek optometry advice. If the long-distance vertical fixation disparity and the long-distance horizontal fixation disparity are both abnormal values, Step S320 is performed to seek customer service, and the exam is stopped. The units of the long-distance vertical fixation disparity and the long-distance horizontal fixation disparity are expressed in the degree of prism, and the normal value is less than 0.254. Any value greater than 0.254 is an abnormal value.

In Step S312, as shown in the long-distance vision examination of FIG. 4, at this time, the long-distance diopter, the long-distance adjustment amplitude, and the long-distance eye position of the user are all normal. Therefore, in the case where the visual parameters are all normal, but both eyes are still unable to generate normal fusion, at this time, the exam should be stopped, and the assistance of an ophthalmologist should be sought to provide appropriate optometry advice.

In Step S320, when the long-distance vertical fixation disparity and the long-distance horizontal fixation disparity are both abnormal values, it means that the near-eye display device 100 cannot correct the visual condition of the user. Therefore, customer service needs to be sought to resolve the issue.

After executing the short-distance vision examination as shown in FIG. 3 and the long-distance vision examination as shown in FIG. 4, the near-eye display device 100 records the vision examination data, including the diopter, the astigmatism, the eye position, and a combination thereof corresponding to the short distance and the long distance, of the user.

After completing the above correction, the vision examination data of the user may be input to the system through the operation interface 160. In some embodiments, the operation interface 160 of the user may be a physical button, so the user may confirm the saving of current data (information may be displayed on a screen or a voice assistant may be used for prompting) by the physical button, and store the current data in the storage element 150, which may be directly read and used by the same user the next time.

The user may also load the vision examination data through the operation interface 160 to adjust the system parameters of the near-eye display device 100 according to the vision examination data, so that the user may skip the examining process, and the system may directly adjust corresponding to the vision examination data of the user. In some embodiments, when the near-eye display device 100 is powered on, the system may directly load the vision examination data to complete the personalized setting of the near-eye display device. The user may also input the vision examination data to the near-eye display device 100 through the operation interface.

In summary, the near-eye display device of the disclosure may examine the vision of the user, obtain the vision examination data of the user, and adjust the parameters of the optical system of the near-eye display device according to the vision examination data of the user, so that the near-eye display device can be correspondingly adjusted to suit users with different visual conditions, so that different users can have better usage experiences.

However, the above are only preferred embodiments of the disclosure and should not limit the scope of the disclosure, that is, any simple equivalent changes and modifications made according to the scope of the claims of the disclosure and the content of the description of the disclosure shall fall within the scope of the disclosure. In addition, it is not necessary for any embodiment of the disclosure or the claimed scope of the disclosure to achieve all of the objectives, advantages, or features disclosed in the disclosure. In addition, the abstract and headings are only used to aid the search of patent documents and are not intended to limit the scope of the disclosure. In addition, terms such as "first" and "second" mentioned in the specification or the scope of the claims are only used to name the elements or to distinguish different embodiments or ranges, and are not used to limit the upper limit or the lower limit of the number of elements.

What is claimed is:

1. A near-eye display device, disposed in front of an eye of a user, the near-eye display device comprising:
    a display, configured to emit an image beam;
    a lens array, disposed on a transmission path of the image beam and located between the display and the eye;
    at least one lens, disposed on the transmission path of the image beam and located between the display and the eye, wherein the image beam is projected to the eye via the lens array and the at least one lens to form a display image; and
    a processor, coupled to the display, wherein the processor is configured to change the display image to perform a short-distance vision examination on the eye, change the display image to perform a long-distance vision examination on the eye, obtain vision examination data of the user according to results of the short-distance vision examination and the long-distance vision examination, and store the vision examination data, and adjust a system parameter of the near-eye display device according to the vision examination data.

2. The near-eye display device according to claim 1, wherein the short-distance vision examination comprises:
    a first short-distance binocular image fusion exam;
    a short-distance diopter exam;
    a short-distance adjustment amplitude exam;
    a short-distance eye position exam; and
    a second short-distance binocular image fusion exam.

3. The near-eye display device according to claim 1, wherein the long-distance vision examination comprises:
    a first long-distance binocular image fusion exam;
    a long-distance diopter exam;

a long-distance eye position exam; and a second long-distance binocular image fusion exam.

4. The near-eye display device according to claim 1, further comprising:

a storage element, configured to store the vision examination data, wherein the processor is further configured to read the vision examination data from the storage element.

5. The near-eye display device according to claim 1, further comprising:

an operation interface, configured to allow the user to input the vision examination data to the near-eye display device through the operation interface, and to load the vision examination data through the operation interface to adjust a system parameter of the near-eye display device according to the vision examination data.

* * * * *